United States Patent [19]

Kulenkampff

[11] Patent Number: 5,093,124
[45] Date of Patent: Mar. 3, 1992

[54] FATTY ACID-BASED PESTICIDE WITH REDUCED PHYTOTOXICITY

[75] Inventor: Hellmut E. Kulenkampff, Hameln, Fed. Rep. of Germany

[73] Assignee: Safer, Inc., Eden Prairie, Minn.

[21] Appl. No.: 439,454

[22] Filed: Nov. 20, 1989

[51] Int. Cl.⁵ .............................................. A01N 25/32
[52] U.S. Cl. ...................................... 424/406; 424/43;
424/195.1; 424/405; 424/409
[58] Field of Search ............... 424/408, 409, 407, 406,
424/410, 195.1, 405, 450; 514/65

[56] References Cited

U.S. PATENT DOCUMENTS

| | | | |
|---|---|---|---|
| 2,825,640 | 3/1958 | Northcraft et al. | 71/2.7 |
| 4,107,292 | 8/1978 | Nemeth | 424/78 |
| 4,381,194 | 4/1983 | DelliColli et al. | 424/406 |

FOREIGN PATENT DOCUMENTS 60-146808  2/1985  Japan .

OTHER PUBLICATIONS

George S. Puritch, Pesticidal Soaps and Adjuvants—What Are They and How Do They Work?, pp. 53–67.

*Primary Examiner*—Thurman K. Page
*Assistant Examiner*—James M. Spear
*Attorney, Agent, or Firm*—Kinney & Lange

[57] ABSTRACT

Disclosed are environmentally compatible pesticidal compositions comprising fungicidally or arthropodicidally effective alpha mono carboxylic acids and their salts having reduced phytotoxicity. The reductions in phytotoxicity are achieved by including in the composition a seaweed extract and/or a lecithin.

15 Claims, No Drawings

FATTY ACID-BASED PESTICIDE WITH REDUCED PHYTOTOXICITY

BACKGROUND OF THE INVENTION

This invention relates to environmentally safe pesticide compositions. Particularly, the invention features pesticidal formulations, particularly fungicidal and arthropodicidal formulations comprising certain mono alpha carboxylic fatty acids and/or their soaps, lecithin, and seaweed extract. The formulations exhibit significant pesticidal activity with a reduction in phytotoxicity. The fungicidal compositions are effective in the control of a broad range of fungi and mosses, are environmentally safe, and are essentially non-toxic to the user.

The use of pesticides has greatly enhanced ornamental and agricultural plant productivity, but it has become apparent that there are limits to the amount of petrochemical-based materials that safely may be absorbed into the environment. Catastrophic, unanticipated, and relatively long term effects experienced with previously used materials have increased the awareness of the potentially dangerous environmental impact on the widespread use of such synthetic pesticides. This has contributed to the creation of regulatory agencies charged with protecting the environment, and has provided the impetus for research for potentially less dangerous pesticidal materials. Salts of fatty acids, primarily sodium or potassium fatty acid soaps, recently have been used commercially as insecticides. Compositions having excellent insecticidal properties which exploit this type of active ingredient are available commercially under the trademark SAFER INSECTICIDAL SOAP. These fatty acid soaps are naturally occurring materials having no known long term environmental effects. They have proven very effective against a variety Of insects, but when applied to plants, particularly at higher concentrations, are somewhat phytotoxic.

Similarly, studies have been initiated to develop a broad-spectrum fatty acid-based fungicide which is non-toxic to the user and environmentally safe. Three types of fatty acid soaps were selected and developed as a fungicide and moss-killer. The formulation is currently sold under the trademark De-Moss. De-Moss TM is an excellent fungicide and moss killer when applied to walkways or painted surfaces, but when applied to flowering decorative plants, shrubs, fruit trees and the like, it can be phytotoxic and has a relatively small useful concentration range. Specifically, the concentration range of De-Moss TM that has acceptably low phytotoxicity but acceptably high fungitoxicity is too restrictive. Below the effective concentration range, fungicidal activity diminishes; above the range, the plant tissue is damaged.

It is an object of this invention to provide pesticidal formulations, i.e., fungicides and insecticides, comprising natural, biodegradable materials which are inexpensive, non-toxic to animals, only mildly toxic to plants, and effective against a broad range of plant pests. Another object is to provide fungicidal, insecticidal, and miticidal compositions which can be applied to the leaves and flora of green plants. Another object is to provide an environmentally safe fungicidal composition comprising an aqueous solution of natural products which has low acceptable phytotoxicity and low cost. Another object is to provide a method of reducing the phytotoxicity of fatty acid based fungicidal, miticidal, and insecticidal solutions.

These and other objects and features of the invention will be apparent from the description and claims which follow.

SUMMARY OF THE INVENTION

It has now been discovered that seaweed extracts may be used in admixture with fatty acid based pesticides to reduce the phytoxicity of the pesticide. It has also been discovered that a reduction in phytotoxicity is observed upon the addition of lecithin to such fatty acid based pesticides. These observations enable provision of a family of fatty acid based pesticidal solutions comprising a mixture of active, readily biodegradable, pesticidal materials formulated to retain pesticidal effectiveness while reducing phytotoxicity. The fungicides are economical to use, toxic to most fungi and arthropods such as insects and mites, substantially non-toxic to animals, and only mildly toxic to plants.

The invention thus provides a biodegradable, aqueous, pesticidal solution for application to the leaves and flora of plants which is effective to control damage from fungal or arthropod pests. The composition comprises a major amount of a fungicidally or arthropodicidally effective first component consisting of one or a mixture of mono alpha carboxylic acids of a hydrocarbon having between 8 and 18 carbon atoms, or an alkali metal salt thereof, and a minor amount of a phytotoxicity-reducing water soluble material such as lecithin, a seaweed extract, or a mixture thereof. Preferably, both a lecithin and a seaweed extract are used in combination with the fatty acid component.

Broadly, the compositions may comprise between 5 and 150 parts lecithin and/or between 2 and 80 parts seaweed extract per 100 parts by weight fatty acid pesticide. Preferred compositions comprise between 10 and 40 parts lecithin and between 5 and 20 parts seaweed extract per 100 parts active. The most preferred compositions comprise about 30 parts lecithin and 10 parts seaweed extract per 100 parts active. Where the solution is designed primarily as a fungicide, the active preferably is a mono alpha carboxylic acid of a hydrocarbon having 7 to 12, preferrably 9 or 10 carbon atoms, again at least partially neutralized by an alkali metal such as potassium. Such fungicidally active compositions may also include coconut oil fatty acids or alkali metal salts thereof. Where the composition is designed primarily as an arthropodicide, the preferred active is mono alpha carboxylic acids of hydrocarbons having between 16 and 18 carbon atoms, preferably, at least partially neutralized with alkali metals. Mixtures of such compositions rich in oleic and/or linoleic acid salts are preferred.

In another aspect, the invention provides a method of reducing phytotoxicity of an aqueous pesticide comprising a fungicide or an arthropodicide. The method consists of the step of mixing the aqueous pesticide with a lecithin, a seaweed extract, or preferably a mixture thereof, in an amount sufficient to reduce the phytotoxicity of the pesticidally active ingredient.

DESCRIPTION

Mono alpha carboxylic acids of saturated or unsaturated carbon chains having 8 to 18 carbon atoms have been used to formulate arthropodicidal solutions effective against insect and arachnid pests as well as fungicidal and moss killing compositions. These materials are naturally occuring and readily biodegradable. Their use as pesticides presents a more environmentally compatible approach to the control of such pests as compared with the widely used petrochemical based pesticides. An arthropodioidal formulation exploiting these active ingredients is commercially available under the trademark SAFER INSECTICIDAL SOAP which, in recent years, has enjoyed enormous commercial success. Fungicidal and moss killing compositions exploiting these active ingredients have been marketed under the tradename DE-MOSS. This product has also enjoyed considerable success.

The commercial arthropodicidal product is sold in ready-to-use form and as a concentrate designed for dilution by the consumer. Its active ingredients comprise longer chain mono alpha carboxylic acids, rich in C16 to C18 components, partially or completely neutralized with alkali metal. The composition of the product varies slightly from batch to batch, but always includes at least about 70% by weight salt (or acid form) oleic acid and at least about 6% salt (or acid form), linoleic acid. The remainder of the product comprise other fatty acids or salts having between 12 and 20 carbon atoms. The ready-to-use formulations (or the concentrate after the recommended 20:1 dilution with water) comprises about 1% fatty acid component. At these levels, the composition is a potent insecticide having very minimal phytotoxicity. However, were the phytotoxic properties of this type of active ingredient to be reduced, higher concentrations of actives and additional improvements in arthropodicidal properties could be obtained.

The commercial fungicidal and moss killing product comprises a mixture of fatty acids or their salts rich in lower molecular weight components. The concentrate comprises approximately 40% by weight active ingredient dissolved in water and includes about 10% pelargonic acid (saturated $C_9$, nonanoic acid), 10% capric acid (saturated $C_{10}$, decanoic acid), and 20% coconut fatty acids, all of which are partially or completely neutralized with a strong base such as potassium hydroxide. The coconut fatty acids comprise: caprylic acid ($C_8$, 7.6%), capric acid ($C_{10}$ 7.3%), lauric acid ($C_{12}$ 48.2%), myristic acid ($C_{14}$, 16.6%) palmitic acid ($C_{16}$, 9.0%), stearic acid ($C_{18}$, 3.8%), oleic acid (unsaturated 9-octadecanoic acid, 5.0%), and linoleic acid (doubly unsaturated 9, 12 octadecanoic acid, 2.5%). The palmitic acid comprises hexadecanoic (8.0%), and cis-9-hexadecanoic (1.0%). This solution, when diluted with water to concentrations of active ingredient of about 0.24% by weight, is an efficient fungicide.

These low molecular weight carboxylic acids and salts are significantly phytotoxic. In fact, compositions rich in the $C_7$ to $C_{12}$ carboxylic acids are useful at higher concentrations as a general herbicide. Accordingly, while this fungicidal product works extremely well when applied to surfaces infected by mosses or fungus, it is useful to control fungal growth on green plants only within a relatively narrow concentration range of about 0.1% to 1.0% by weight. If used as a more dilute solution, the material's fungicidal properties deteriorate. At higher concentrations, the risk of damaging the plant increases.

It has now been discovered that two types of natural, plant-derived materials may be added to such compositions individually or preferably together to provide a pesticidal mixture having very significantly reduced phytotoxicity. The phytotoxicity reducing components are lecithin and seaweed suspensions. Use of these materials permits the application of more concentrated fatty acid based arthropodicidal solutions to plants and increases the window of utility of the fungicidal composition for application to plants.

The lecithins are mixtures of diglycerides of fatty acids linked to the choline ester of phosphoric acid. Pure lecithin is phosphatidyl choline. These phospholipids are widely commercially available in various forms derivable from soybean oil, corn and other vegetable seeds, as well as animal sources such as egg yolk. Lecithins are environmentally safe and often used as food additives. A preferred type of lecithin is soybean lecithin available from several commercial sources.

Seaweeds such as *Ascophyllum nodosum* grows in northern oceans and are harvested commercially. Extracts of their water-soluble components are available commercially under the trade name Algan from PB Ohrstrom & Sons, Inc. This product is an aqueous extract comprising about 30% by weight *Ascophyllum nodosum*. Other useful extracts are available from Bio-Crop International of Concord, Ontario, Canada under the trade name Micro Mist 300 and from Atlantic Laboratories of Waldoboro, Maine under the trade name Seaplant Extract. It is not currently known what component of those seaweed products are responsible for the observed reductions in phytotoxicity. However, neither the alginate content nor the cytokinin content alone appear to be the result-effective material.

Each of lecithin and seaweed extract individually has been observed to reduce significantly the phytotoxicity of pesticidally active monocarboxylic fatty acids of the types described above. Each component may be used individually for this purpose, but preferably the two are used in combination. Neither component appears to reduce significantly the fungicidal or arthropodicidal activity of the active fatty acid ingredients.

The phytotoxicity reducing lecithin or seaweed extract components may be used in essentially any weight ratio with the active that produces a solution at the concentration of use. Of course, very low amounts of the lecithins or extracts induce only low or often undetectable decreases in phytotoxicity. Very high concentrations can present solubility difficulties and are generally not cost effective. The broadly preferred compositions comprise between 5 and 150 parts lecithin or between 2 and 80 parts seaweed extract per 100 parts active carboxylic acid. More preferred compositions comprises both lecithin and seaweed extract present at levels between 10 and 40 parts lecithin and between 5 and 20 parts seaweed extract per 100 parts active. The currently preferred solution comprises 100 parts active, about 30 parts lecithin, and about 10 parts seaweed extract.

The compositions are manufactured simply by mixing together the various components in aqueous solution. They are used by spraying or otherwise applying aqueous solutions of a desired dilution to the leaves and flora of plants to protect the plants from fungal growth or arthropod infestation. The novel fungicides may be applied to plants at between about 0.1% to about 2.0% by weight or higher. The preferred active content is 0.1% to 1.0% by weight, and the most preferred is about 0.25% by weight. The insecticidal product may be applied to plants at any percent active below about 5.0% by weight, but . preferably is between 0.1% and 2.0%, and most preferably about 1.0%. Of course, higher concentration of actives may be used on inert surfaces. These products exhibit a combination of fungicidal and/or arthropodicidal activity, spectrum response, low phytotoxicity, and ready biodegradability unavailable in any composition known to applicants.

The following examples illustrate the reduction in phytotoxicity and the efficiency of the pesticidal compositions of the invention.

EXAMPLE 1

DEMONSTRATION OF PHYTOTOXICITY REDUCTION

Fourteen-day old greenhouse-grown bean plants (*Phaseolus vulgaris*, variety Pinto) are sprayed to run-off with solutions of a composition set forth below. Seventy-two hours after spraying, the necrotic area of the primary true leaves of every plant is measured using a standard phytotoxicity assessment procedure, i.e., proportion of necrotic leaf area. The results, nature of the solutions used, and concentrations used, are set forth in the table below. In the table, the actives comprise a solution identical to the De-Moss product disclosed above comprising one part pelargonic acid, one part capric acid, and two parts coconut fatty acids, neutralized with potassium hydroxide. The seaweed extract used is the product sold commercially under the trade name Algan. The lecithin used in each case comprised soybean lecithin. All proportions are by weight.

TABLE 1

| A. Active Plus Seeweed Extract | | |
|---|---|---|
| Test Series | Active Conc. (%) | Parts Extract per 100 parts active | Percent Phytotoxicity |
| 1 | 5.4 | 0 | 54.5 |
| | 5.4 | 4.6 | 24.9 |
| | 5.4 | 9.26 | 30.7 |
| | 5.4 | 18.5 | 23.4 |
| 2 | 3.6 | 0 | 56.9 |
| | 3.6 | 6.9 | 46.0 |
| | 3.6 | 13.8 | 29.0 |
| | 3.6 | 27.7 | 10.1 |
| 3 | 2.9 | 0 | 54.6 |
| | 2.9 | 8.6 | 25.8 |
| | 2.9 | 17.3 | 23.5 |
| | 2.9 | 34.7 | 22.5 |
| | 2.9 | 69.4 | 8.9 |
| 4 | 2.4 | 0 | 13.2 |
| | 2.4 | 10.4 | 5.3 |
| | 2.4 | 20.8 | 4.6 |
| | 2.4 | 41.6 | 4.1 |
| | 2.4 | 83.3 | 2.3 |
| 5 | 2.4 | 0 | 28.8 |
| | 2.4 | 10.4 | 25.2 |
| | 2.4 | 20.8 | 12.4 |
| | 2.4 | 41.6 | 13.4 |
| | 2.4 | 83.3 | 11.2 |

| B. Active Plus Lecithin | | |
|---|---|---|
| Test Series | Active Conc. (%) | Parts lecithin per 100 parts active | Percent Phytoxticity |
| 1 | 5.4 | 0 | 54.5 |
| | 5.4 | 9.26 | 39.1 |
| | 5.4 | 18.5 | 32.3 |
| | 5.4 | 37.0 | 32.9 |
| 2 | 3.6 | 0 | 56.9 |
| | 3.6 | 13.8 | 33.3 |
| | 3.6 | 27.7 | 37.8 |
| | 3.6 | 55.5 | 25.6 |
| 3 | 2.9 | 0 | 54.6 |
| | 2.9 | 17.4 | 22.1 |
| | 2.9 | 34.7 | 40.8 |
| | 2.9 | 69.4 | 24.3 |
| | 2.9 | 139 | 23.0 |
| 4 | 2.4 | 0 | 13.2 |
| | 2.4 | 20.8 | 5.5 |
| | 2.4 | 41.6 | 4.9 |
| | 2.4 | 83.3 | 3.4 |

TABLE 1-continued

| | | |
|---|---|---|
| | 2.4 | 166 | 2.1 |
| 5 | 2.4 | 0 | 28.8 |
| | 2.4 | 20.8 | 15.2 |
| | 2.4 | 41.6 | 17.9 |
| | 2.4 | 83.3 | 17.1 |
| | 2.4 | 166 | 10.4 |
| Control run with each test series (water) | | |
| | 0 | 0 | 0 |

As illustrated by the data, within each test run, reductions in phytotoxicity uniformly are observed using active concentrations ranging between 5.4% and 2.4% by weight in mixture with seaweed extract ranging between 4.6 and 83.3 parts per 100 parts active, and lecithin contents ranging between 9.26 and 166 parts lecithin per 100 parts active.

EXAMPLE 2

PREFERRED FORMULATION

The phytotoxicity of various concentrations of 1) active ingredient (De-Moss) and 2) the preferred low phytotoxicity fungicidal compositions of the invention were assessed as set forth below. The preferred formulation, identified as "NV", comprises 100 part De-Moss, about 30 parts soybean lecithin, and about 10 parts seaweed extract. Water controls run in parallel with the tests showed zero phytotoxicity in all cases phytotoxicity was again measured by assessing the fraction of necrotic leaf area using a standard protocol. The tests were repeated at various times using various plant species including *Phaseoleous vulgaris* variety pinto. *Tagetes patula*, variety petite Harmony (marigold), and *Tropaeolum majus*, variety Whirlybird (nasturtium). IN each case, 14 day old greenhouse grown plants were sprayed to run off with currently preferred composition of the invention (NV) and the De-Moss composition. Concentration in each case is expressed as percent active monocarboxylic fatty acids (or salt form) in the respective compositions. The results are set forth in Table 2 below.

TABLE 2

| Test No. | Test Composition | Active Conc. (%) | Percent Phytotoxicity |
|---|---|---|---|
| 1 | NV | 0.36 | 1.2 |
| | DM | 0.36 | 3.2 |
| 2 | NV | 0.36 | 0.5 |
| | DM | 0.36 | 0.0 |
| 3 | NV | 0.54 | 4.3 |
| | DM | 0.54 | 11.0 |
| 4 | NV | 0.72 | 13.1 |
| | DM | 0.72 | 20.5 |
| 5 | NV | 0.72 | 0.3 |
| | DM | 0.72 | 1.9 |
| 6 | NV | 1.4 | 17.0 |
| | DM | 1.4 | 55.4 |
| 7 | NV | 1.4 | 2.8 |
| | DM | 1.4 | 4.0 |
| 8 | NV | 1.4 | 3.6 |
| | DM | 1.4 | 9.1 |
| 9 | NV | 1.4 | 7.0 |
| | DM | 1.4 | 10.5 |
| 10 | NV | 1.4 | 11.3 |
| | DM | 1.4 | 12.8 |
| 11 | NV | 1.4 | 1.7 |
| | DM | 1.4 | 3.6 |
| 12 | NV | 1.4 | 3.3 |
| | DM | 1.4 | 4.5 |
| 13 | NV | 2.8 | 70.8 |
| | DM | 2.8 | 86.1 |
| 14 | NV | 2.8 | 9.0 |

TABLE 2-continued

| Test No. | Test Composition | Active Conc. (%) | Percent Phytotoxicity |
|---|---|---|---|
|  | DM | 2.8 | 15.5 |
| 15 | NV | 2.8 | 17.7 |
|  | DM | 2.8 | 21.8 |
| 16 | NV | 2.8 | 27.0 |
|  | DM | 2.8 | 51.3 |
| 17 | NV | 2.8 | 23.0 |
|  | DM | 2.8 | 32.0 |
| 18 | NV | 2.8 | 5.8 |
|  | DM | 2.8 | 17.7 |
| 19 | NV | 2.8 | 13.4 |
|  | DM | 2.8 | 20.2 |
| 20 | NV | 5.5 | 26.5 |
|  | DM | 5.5 | 50.0 |
| 21 | NV | 5.5 | 29.0 |
|  | DM | 5.5 | 51.0 |

As is illustrated by the foregoing data, use of a mixture of lecithin and seaweed extract with the active mixture of alpha mono carboxylic acids uniformly significantly reduce phytotoxicity.

EXAMPLE 3

EFFICACY

To assess the fungicidal activity of compositions of the invention, an experiment was developed to assess the degree of control in the development of lesions incited by the fungus *Botrytis cinerea* on the susceptible plant *Phaseolus vulgaris*, variety pinto. Solutions of active ingredient alone (DM), the preferred composition of the invention (NV) and water (W) were sprayed to run off on 14 day old greenhouse grown plants. Ten plants were used for each treatment. Tap water was used as a diluent and as a control. Two hours after spraying, the plants were sprayed with a suspension of conidia of *Botrytis cinerea* and placed in a clear plastic tent under conditions of high humidity. The fungus suspension was prepared by growing an isolate of the fungus, obtained from a rotting bean plant, on potato dextrose agar for twenty-one days. The culture was immersed in a nutrient solution (10% sucrose, 0.4% $NaNO_3$, 0.1% $KH_2PO_4$, 89.4% sterile tap water) and gently scraped with a sterile scapel. The solution was filtered through four layers of cheese cloth and diluted with additional nutrient solutions to produce a concentration of about $10^4$ conidia per milliliter of solution. Above the tent a bank of fluorescent tubes provided continual illumination. Every day the plants were exposed to six one-half hour of periods of mists. The mist was generated by an ultrasonic humidifier.

after three days of high humidity, the number of lesions incited on every true primary leaf was recorded. The results are summarized in Table 3 set forth below.

TABLE 3

| Test No. | Ingredients | Active Conc. (%) | Lesions/leaf |
|---|---|---|---|
| 1 | NV | .36 | 20.0 |
|  | DM | .36 | 19.0 |
|  | W | 0 | 36.0 |
| 2 | NV | .36 | 2.1 |
|  | DM | .36 | 1.5 |
|  | W | 0 | 60.0 |
| 3 | NV | .36 | 6.5 |
|  | DM | .36 | 7.8 |
|  | W | 0 | 32.3 |

From the foregoing it is apparent that the presence of the lecithin and extract in the compositions has no significant effect on their fungicidal activity.

Other embodiments are within the following claims.

What is claimed is:

1. A biodegradeable, aqueous pesticidal solution for application to the leaves and flowers of plants for controlling damage from arthropod or fungal pests, the composition comprising:

an amount of a first component selected from the group consisting of a mono alpha carboxylic acid of a hydrocarbon having between 8 and 18 carbon atoms, alkali metal salts thereof, and mixtures thereof, wherein the amount of the first component is effective as an arthropodicide or a fungicide; and an amount of a second component selected from the group consisting of lecithin, a seaweed extract, and a mixture thereof, said lecithin being present at about 0.05 to 1.5 parts per part of the first component and said seaweed extract being present at 0.02 to 0.8 parts per part of the first component, wherein the amount of the second component is effective to reduce phytotoxicity of the first component.

2. The solution of claim 1 comprising both a lecithin and said seaweed extract.

3. The solution of claim 2 comprising between 0.1 and 0.4 parts lecithin and between 0.05 and 0.2 parts seaweed extract per part of said first component.

4. The solution of claim 3 comprising about 30 parts lecithin, 10 parts said seaweed extract, and 100 parts said first component.

5. The solution of claim 1 wherein said first component comprises an arthropodicidally active mono alpha carboxylic acid of a hydrocarbon having between 16 and 18 carbon atoms, alkali metal salts thereof, and mixtures thereof.

6. The solution of claim 5 wherein said first component comprises oleic acid, linoleic acid, or an alkali metal salt thereof.

7. The solution of claim 1 wherein said first component comprises a fungicidally active mono alpha carboxylic acid of a hydrocarbon having 7 or 12 carbon atoms, alkali metal salts thereof, or a mixture thereof.

8. The solution of claim 7 further comprising a mixture of coconut oil fatty acids, alkali metal salts thereof, or mixtures thereof.

9. The solution of claim 7 wherein said first component has 9 or 10 carbon atoms.

10. A biodegradeable fungicidal composition comprising an aqueous mixture of:

a first component of nonanoic acid, decanoic acid, coconut oil fatty acids having 8-18 carbon atoms, alkali metals salts thereof, or a mixture of the salt and acid form of said acids;

about 0.02 to 0.8 parts of seaweed extract per part of the first component; and 0.05 to 1.5 parts of lecithin per part of the first component.

11. The compositions of claim 10 comprising about 0.3 parts lecithin and about 0.1 parts seaweed extract per part of said first component.

12. A method of reducing the phytotoxicity of an aqueous fatty acid-based pesticide selected from the group consisting of a mono alpha carboxylic acid of a hydrocarbon having between 8 and 18 carbon atoms, alkali metal salts thereof, and mixtures thereof comprising mixing an amount of said aqueous fatty acid-based pesticide with an amount of a material selected from the group consisting of lecithin, a seaweed extract and mixtures thereof, said lecithin being present at about 0.05 to 1.5 parts per part of the aqueous pesticide and said seaweed extract being present at 0.02 to 0.8 parts per part of the aqueous pesticide, wherein the amount of the second component is effective to reduce phytotoxicity of the first component.

13. The method of claim 12 wherein both a said seaweed extract and lecithin are added to said pesticide.

14. The method of claim 12 wherein between 0.05 and 1.0 parts lecithin are added per part said pesticide.

15. The method of claim 12 wherein between 0.02 and 0.5 parts said seaweed extract are added per part said pesticide.

* * * * *